United States Patent
Robinson

(10) Patent No.: US 9,149,499 B1
(45) Date of Patent: Oct. 6, 2015

(54) CANNABIS BASED THERAPEUTIC AND METHOD OF USE

(71) Applicant: Bradley C. Robinson, North Salt Lake, UT (US)

(72) Inventor: Bradley C. Robinson, North Salt Lake, UT (US)

(73) Assignee: Predictive Therapeutics, LLC, North Salt Lake, UT (US)

( * ) Notice: Subject to any disclaimer, the term of this patent is extended or adjusted under 35 U.S.C. 154(b) by 39 days.

(21) Appl. No.: 14/281,172

(22) Filed: May 19, 2014

Related U.S. Application Data

(60) Provisional application No. 61/825,587, filed on May 21, 2013.

(51) Int. Cl.
| | |
|---|---|
| *A01N 65/00* | (2009.01) |
| *A61K 36/185* | (2006.01) |
| *A61K 31/57* | (2006.01) |
| *A61K 31/352* | (2006.01) |
| *A61K 45/06* | (2006.01) |
| *A61K 36/00* | (2006.01) |

(52) U.S. Cl.
CPC .............. *A61K 36/185* (2013.01); *A61K 31/352* (2013.01); *A61K 31/57* (2013.01); *A61K 36/00* (2013.01); *A61K 45/06* (2013.01)

(58) Field of Classification Search
CPC ....................................................... A61K 36/00
USPC ......................................................... 424/725
See application file for complete search history.

(56) References Cited

U.S. PATENT DOCUMENTS

| | | | |
|---|---|---|---|
| 2005/0101579 A1 | 5/2005 | Shippen | 514/167 |
| 2006/0246135 A1 | 11/2006 | Nagi et al. | 424/469 |
| 2008/0306034 A1 | 12/2008 | Ward | 514/170 |
| 2009/0170823 A1 | 7/2009 | Diliberti | 514/171 |

OTHER PUBLICATIONS

Ampio Pharmaceuticals, Prospectus Supplement, Ampio Website, 2011, pp. 1-10.
Lilic et al, Genesis, clinical Presentation, Diagnosis and Treatment of Uterine Myomas, ACTA, 2007, pp. 33-40.
Nasser et al, Management of Pelvic Pain from Dysmenorrhea or Endometriosis, JABFP, 2004, pp. S43-S47.
Schweppe, KW, The Current Place of Progestins in the Treatment of Endometriosis, Obstet Gynecol., 2012, pp. 1-11.
Wieser et al, Sulindac Suppresses Nuclear Factor-kB Activation and RANTES Gene and Protein Expression in Endometrial Stroma Cells from Women with Endometriosis, JCEM, 2005, pp. 6441-6447.
Rodriguez, GC et al, NSAIDs, and progestins synergistically enhance cell death in ovarian epithelial cells, AJOG, Mar. 2012, pp. 253e1-253e9.

*Primary Examiner* — Michael Meller
(74) *Attorney, Agent, or Firm* — Michael R. Schramm

(57) ABSTRACT

The present invention is a compound comprising a cannabis portion and at least one of a progestin portion and a progesterone portion. The compound may optionally also include an NSAID component. The compound may take for instance the form of a pill or pellet (for oral internal use or for subdermal implantation), an injectable solution, or a suppository. The compound is intended for use in treating subjects having or being at increased risk—especially genetically determined risk—of developing endometriosis. The compound may also be used for treating other disorders or as a contraceptive.

1 Claim, No Drawings

CANNABIS BASED THERAPEUTIC AND METHOD OF USE

CROSS REFERENCE TO RELATED APPLICATIONS

This US nonprovisional utility patent application claims the benefit under 35 USC §119(e) of U.S. provisional application No. 61/825,587 filed May 21, 2013 which is expressly incorporated herein in its entirety by this reference.

FIELD OF THE INVENTION

The present invention relates to therapeutics, and more especially cannabis based therapeutics for use in treating those known to have or be at increased risk of endometriosis and other ailments.

BACKGROUND OF THE INVENTION

Endometriosis is a common gynecological disorder. Many therapeutics including progestins and uses of such therapeutics in the treatment of endometriosis are well known. Examples of such therapeutics and methods are taught in US patent application 20080306034 to Ward and in U.S. patent application Ser. No. 13/788,913 to Ward et al. which are incorporated herein in their entirety by this reference. Further, it has been shown that the concurrent administration of both an NSAID (Nonsteroidal Anti-Inflammatory Drug) and a progestin can provide an increased synergistic effect in the treatment of a disorder as compared to what might be obtained by the administration of an NSAID and/or a progestin separately. Moreover, such concurrent administration may allow for reduced dosages of an NSAID and/or a progestin as compared to a required dosage of an NSAID and a progestin administered separately. An example of such concurrent administration is taught in "Rodriguez, G C et al, NSAIDs and progestins synergistically enhance cell death in ovarian epithelial cells, AJOG, March 2012, pg 253e1-253e9" which is incorporated herein in its entirety by this reference. It is further known that cannabis has been shown to reduce pain and/or reduce sensitivity to pain and may have fewer or none of the side effects of other NSAIDs (see Appxs A and B).

SUMMARY OF THE INVENTION

The present invention is a compound comprising a cannabis portion and at least one of a progestin portion and a progesterone portion. The compound may optionally also include an NSAID portion (in addition to and separate from the cannabis based portion). For the purposes of this invention, where reference is used to an NSAID, unless indicated otherwise, such NSAID shall be understood to be a separate and distinct component from a cannabis component. The compound may take for instance the form of a pill or pellet (for oral internal use or for subdermal implantation), an injectable solution, or a suppository. The compound is intended for use in treating subjects having or being at increased risk—especially genetically determined risk—of developing endometriosis. The compound may also be used for treating other disorders such as chronic pain, and more especially chronic pelvic pain or as a contraceptive.

DETAILED DESCRIPTION OF THE INVENTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are included to provide a thorough understanding of embodiments of the invention. One skilled in the relevant art will recognize, however, that the invention can be practiced without one or more of the specific details, or with other methods, components, materials, and so forth. In other instances, well-known structures, materials, or operations are not shown or described in detail to avoid obscuring aspects of the invention.

A first embodiment of the invention is a therapeutic compound for use in treating endometriosis and like disorders and preferably in pill form comprising a compound including a cannabis component and at least one of a progestin component and a progesterone component. The compound may optionally also include an NSAID component. In practice, a subject being determined to have endometriosis or at increased risk of developing endometriosis, and more especially being determined to be genetically predisposed to increased risk of developing endometriosis, is orally administered a therapeutically effective amount of the compound so as to alleviate, cure, or prevent the symptoms of endometriosis. The therapeutic compound may be likewise administered for use as a contraceptive.

A second embodiment of the invention is a therapeutic compound for use in treating endometriosis and like disorders and preferably in pellet form comprising a compound including a cannabis component and at least one of a progestin component and a progesterone component. The compound may optionally also include an NSAID component. In practice, a subject being determined to have endometriosis or at increased risk of developing endometriosis, and more especially being determined to be genetically predisposed to increased risk of developing endometriosis, is administered a therapeutically effective amount of the compound by implanting the compound subdermally into the subject so as to alleviate, cure, or prevent the symptoms of endometriosis. The therapeutic compound may be likewise administered for use as a contraceptive.

A third embodiment of the invention is a therapeutic compound for use in treating endometriosis and like disorders and preferably in solution form comprising a compound including a cannabis component and at least one of a progestin component and a progesterone component. The compound may optionally also include an NSAID component. In practice, a subject being determined to have endometriosis or at increased risk of developing endometriosis, and more especially being determined to be genetically predisposed to increased risk of developing endometriosis, is administered a therapeutically effective amount of the compound by injecting the compound subdermally into the subject so as to alleviate, cure, or prevent the symptoms of endometriosis. The therapeutic compound may be likewise administered for use as a contraceptive.

A fourth embodiment of the invention is a therapeutic compound for use in treating endometriosis and like disorders and preferably in suppository form comprising a compound including a cannabis component and at least one of a progestin component and a progesterone component. The compound may optionally also include an NSAID component. In practice, a subject being determined to have endometriosis or at increased risk of developing endometriosis, and more especially being determined to be genetically predisposed to increased risk of developing endometriosis, is administered a therapeutically effective amount of the compound by placing the compound into a body orifice of the subject (e.g. vaginally or rectally) so as to alleviate, cure, or prevent the symptoms of endometriosis. The therapeutic compound may be likewise administered for use as a contraceptive.

It shall be noted that the progestin disclosed herein may include any of a first generation progestin (estrane) including norethindrone, norethynodrel, norethindrone acetate, and ethynodiol diacetate, a second generation progestin (gonane) including levonorgestrel, norethisterone, and norgestrel, a third generation progestin (gonane) including desogestrel, gestodene, norgestimate, drospirenone, and a fourth generation progestin including dienogest, nestorone, nomegestrol acetate, and trimegestone. It shall also be noted that the progesterone disclosed herein may include tanaproget. It shall also be noted that the cannabis component is preferably free of a THC portion. It shall also be noted that the cannabis component may include any of a nabilone, dronabinol, and nabiximols. It shall also be noted that the NSAID disclosed herein may include any of a salicylate including aspirin (acetylsalicylic acid), diflunisal, and salsalate, a propionic acid derivative including ibuprofen, dexibuprofen, naproxen, fenoprofen, ketoprofen, dexketoprofen, flurbiprofen, oxaprozin, and loxoprofen, an acetic acid derivative including indomethacin, tolmetin, sulindac, etodolac, ketorolac, diclofenac, and nabumetone, an enolic acid (oxicam) derivative including piroxicam, meloxicam, tenoxicam, droxicam, lornoxicam, and isoxicam, a fenamic acid derivative (fenamates) including efenamic acid, meclofenamic acid, flufenamic acid, and tolfenamic acid, a selective COX-2 inhibitor (Coxibs) including celecoxib, rofecoxib, valdecoxib, parecoxib, lumiracoxib, etoricoxib, and firocoxib (used in dogs and horses), a sulphonanilide including nimesulide, an other NSAID including licofelone (acts by inhibiting LOX (lipooxygenase) & COX and hence known as LOX/COX inhibitor) and lysine clonixinate, and a natural NSAID including hyperforin, figwort, and calcitriol (vitamin D). It shall also be noted that the compound disclosed herein may include a biologic component including AMPION. It shall also be noted that the therapeutic compound disclosed herein is also useful in increasing dosage accuracy and administration convenience as compared to concurrent administration of separate NSAID and progestin and/or progesterone components.

An exemplary therapeutic compound conforming with any of the disclosed embodiments may comprise for instance a compound including at least one of nabilone, dronabinol, and nabiximols, and at least one of a progestin component and a progesterone component and optionally at least one of naproxen, meloxicam, and celecoxi. A further exemplary therapeutic compound conforming with any of the disclosed embodiments may comprise for instance a compound including at least one of nabilone, dronabinol, and nabiximols and at least one of a progestin component and a progesterone component and optionally at least one of piroxicam, sulindac, and nabumetone. Still further an exemplary therapeutic compound conforming with any of the disclosed embodiments may comprise for instance a compound including 200 to 400 mg (milligrams) of nabilone and 250 to 450 µg (micrograms) of norethindrone preferably administered as a once daily dosage. Still further an exemplary therapeutic compound conforming with any of the disclosed embodiments may comprise for instance a compound including 200 to 400 mg (milligrams) of nabilone and 250 to 450 µg (micrograms) of norethindrone preferably administered as a once daily dosage. Still further an exemplary therapeutic compound conforming with any of the disclosed embodiments may comprise for instance a compound including approximately 300 mg of nabilone and approximately 350 µg of norethindrone preferably administered as a once daily dosage.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A pharmaceutical pill or subdermally implantable pellet for treating a human suffering from endometriosis consisting essentially of therapeutically effective amounts of a component selected from the group consisting of norethindrone, norethynodrel, norethindrone acetate, ethynodiol diacetate, levonorgestrel, norethisterone, norgestrel, desogestrel, gestodene, norgestimate, drospirenone, dienogest, drospirenone, nestorone, nomegestrol acetate, and trimegestone, a component selected from the group consisting of nabilone, dronabinol and nabiximol and tanaproget.

* * * * *